(12) United States Patent
Berger

(10) Patent No.: US 9,637,529 B2
(45) Date of Patent: May 2, 2017

(54) MEDICAMENT FOR ATROPHY TREATMENT OR INCREASING CELL GROWTH

(71) Applicant: SIMU TRADE CONSULTING GMBH & CO. LEASING KG, Vienna (AT)

(72) Inventor: Rudolf Berger, Krems (AT)

(73) Assignee: SIMU TRADE CONSULTING GMBH & CO. LEASING KG, Vienna (AT)

(*) Notice: Subject to any disclaimer, the term of this patent is extended or adjusted under 35 U.S.C. 154(b) by 0 days.

(21) Appl. No.: 14/651,809

(22) PCT Filed: Dec. 13, 2013

(86) PCT No.: PCT/EP2013/076547
§ 371 (c)(1),
(2) Date: Jun. 12, 2015

(87) PCT Pub. No.: WO2014/090991
PCT Pub. Date: Jun. 19, 2014

(65) Prior Publication Data
US 2015/0307568 A1    Oct. 29, 2015

(30) Foreign Application Priority Data

Dec. 14, 2012   (EP) .................... 12197192

(51) Int. Cl.
| | | |
|---|---|---|
| A61K 38/00 | (2006.01) | |
| C07K 14/47 | (2006.01) | |
| A61K 31/00 | (2006.01) | |
| A61K 38/17 | (2006.01) | |

(52) U.S. Cl.
CPC .............. *C07K 14/47* (2013.01); *A61K 31/00* (2013.01); *A61K 38/1709* (2013.01)

(58) Field of Classification Search
None
See application file for complete search history.

(56) References Cited

PUBLICATIONS

Bennani-Baiti et al., Support Care Cancer (2011) vol. 19, pp. 1451-1463.*
Written Opinion EPO [PCT/EP2013/076547] dated Jun. 19, 2014.
Van Ham Tjakko J et al. "Indentification of MOAG-4/SERF as a Regulator of Age-Related Proteotoxicity", Cell, vol. 142, No. 4, Aug. 2010 (Aug. 2010), pp. 601-612.
Database Geneseq [Online] Oct. 4, 2007 (Oct. 4, 2007), "Human protein, SEQ ID 1143" retrieved from EBI accession No. GSP:AGI32189 Database accession No. AGI321189 & us 20070432392 a1 (Tang YT [US] et al) 22 Feebruary 2007 (Feb. 22, 2007).
Database Geneseq [Online] Mar. 9, 2001 (Mar. 9, 2001), "Human colon cancer antigen protein sequence SEQ ID No. 1054" retrieved from EBI accession No. GSP:AAB53514 Database accession No. AAB53514.
Office Action EP12197192.3 dated May 17, 2013.
Marzetti Emanuele et al: "Apoptosis in Skeletal Myocytes: A Potential Target for Interventions against Sarcopenia and PhysicaL Fraillty—A Mini-Review", Gerontology, vol. 58, No. 2, Sep. 23, 2011 (Sep. 23, 2011), pp. 99-106, XP002696502, ISSN:0304-324X the whole document.

* cited by examiner

*Primary Examiner* — Jim Ketter
(74) *Attorney, Agent, or Firm* — Chainey P. Singleton; Edwin S. Flores; Chalker Flores, LLP

(57) ABSTRACT

The present invention provides SERF2, a nucleic acid encoding said SERF2 or a cell expressing SERF2 for use as a medicament, in particular for use for use in treating or preventing an atrophy disease or condition or for increasing cellular growth in a patient such as sarcopenia, cachexia, dystrophy, hypoplasia, hypotonia, or muscle loss, as well as in vitro methods suitable for cell culture proliferation and pharmaceutical compositions.

15 Claims, 13 Drawing Sheets

A: PBS

B: VEGF

C: SERF2

SEQUENCE LISTING

```
<160> NUMBER OF SEQ ID NOS: 2

<210> SEQ ID NO 1
<211> LENGTH: 59
<212> TYPE: PRT
<213> ORGANISM: homo sapiens

<400> SEQUENCE: 1

Met Thr Arg Gly Asn Gln Arg Glu Leu Ala Arg Gln Lys Asn Met Lys
1               5                   10                  15

Lys Gln Ser Asp Ser Val Lys Gly Lys Arg Arg Asp Asp Gly Leu Ser
            20                  25                  30

Ala Ala Ala Arg Lys Gln Arg Asp Ser Glu Ile Met Gln Gln Lys Gln
        35                  40                  45

Lys Lys Ala Asn Glu Lys Lys Glu Glu Pro Lys
    50                  55

<210> SEQ ID NO 2
<211> LENGTH: 180
<212> TYPE: DNA
<213> ORGANISM: homo sapiens

<400> SEQUENCE: 2
atgacccgcg gtaaccagcg tgagctcgcc cgccagaaga atatgaaaaa gcagagcgac     60
tcggttaagg gaaagcgccg agatgacggg ctttctgctg ccgcccgcaa gcagagggac    120
tcggagatca tgcagcagaa gcagaaaaag gcaaacgaga agaaggagga acccaagtag    180
```

MEDICAMENT FOR ATROPHY TREATMENT OR INCREASING CELL GROWTH

FIELD OF THE INVENTION

Figure 1:
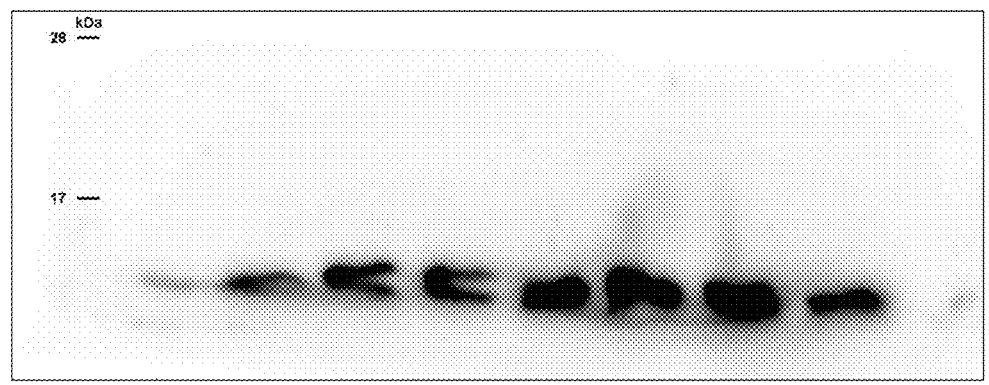

The present invention relates to the field of drugs for regenerative treatments, in particular for regeneration of muscle cells and mitigation of programmed cell death in human cells of various origins.

BACKGROUND

Predominant diseases characterized by a lack of regeneration of cells or deregulated apoptosis are sarcopenia and cachexia. The etiology of sarcopenia is multifactorial but still poorly understood while the sequelae of this phenomenon, i.e. loss of independence and metabolic complications, represent a major public health problem. The most evident metabolic explanation for muscle decline in elderly people is an imbalance between protein synthesis and breakdown rates but other causes like disproportionately increased rate of programmed cell death (apoptosis), neurodegenerative processes, reduction in anabolic hormone productions or sensitivity such as insulin, growth and sex hormones, dysregulation of cytokine secretions, modification in the response to inflammatory events, inadequate nutritional intakes and sedentary lifestyle are involved. A multimodal approach combining nutrition, exercise, hormones, specific anabolic drugs may be treatment regimens for limiting the development of sarcopenia with aging. However, all therapy approaches have severe disadvantages, for instance hormones and anabolic drugs often have severe side effects. A consensus definition of sarcopenia is disclosed in von Haehling et al., J Cachexia Sarcopenia Muscle (2010) 1:129-133.

Sarcopenia and lack of physical activity are connected. However, physical activity alone cannot prevent sarcopenia completely. Treatment strategies of sarcopenia are unsatisfying. The most common therapies are application of hormones that interact with muscle growth such as testosterone. Unfortunately, it has been shown that treatment with testosterone may induce a variety of side effects such as cardiovascular diseases or cancer.

Sarcopenia is usually seen in elderly people, but can also be observed in young adults, like dementia. The prevalence of sarcopenia in 60-70 year old people is 5-11%, whereby in people over 80 years it is 11-50%. It is estimated that 200 million people will suffer from this syndrome over the next 30 years (Cruz-Jentoft A., Age and Ageing 2010, 39).

Not only people with age-related sarcopenia are affected, but also patients being bedridden, having tumors or people without physical activity have a marked decrease of muscle tissue. The enormous costs for the health care system for these patients together with the fast increase of the aging population and concomitantly the increase of age-related sarcopenia demands an efficient therapy for sarcopenia.

Cachexia is defined as physical wasting with loss of muscle mass and weight that is caused by disease. It is common for elderly individuals who have disease to exhibit cachexia. Additionally, muscle mass loss is characteristic of the conditions of frailty and sarcopenia. Physical frailty is a condition that results from reduced strength, reduced gait velocity, reduced physical activity, weight loss, and exhaustion. Sarcopenia and frailty could be classified as cachectic conditions because they are associated with muscle mass loss.

Apoptosis describes the so called programmed cell death, which is an active process by which cells get destructed. This destruction undergoes some characteristic morphological changes, like chromatin condensation, cell shrinkage, membrane blebbing, and formation of apoptotic bodies. It is known, that the cells in the adult body are in a perfect balance between cell division and controlled cell death. There are different events where apoptosis occurs, e.g. in the formation of fingers and toes in the human embryonic development or when cells are degenerated, nonfunctional and/or potentially dangerous to the animal. Apoptosis is characterized by a controlled sequence of events. The first sign is condensation of chromatin, DNA-fragmentation, expression of proteolytic enzymes and finally cell destruction. These biochemical and morphological changes can be measured with different methods, whereat it is very important to choose examination methods, which are able to distinguish between apoptosis and necrosis, because some of them just detect cell death in general.

Available evidence suggests that targeting myonuclear apoptosis provides novel and effective therapeutic tools to combat sarcopenia (Marzetti E. et al. (2012) Gerontology 58/2:99-106). Since loss of muscle cell mass is a serious problem for elderly people it would be of great importance to provide a therapy that regains muscle strength for these patients. Muscle cell loss is also known as sarcopenia. There is currently no satisfying therapy for this disease and induction of muscle cell growth might lead to a new and innovative therapy for sarcopenia. Muscle cell loss results from an imbalance between cell division and controlled cell death (apoptosis).

It is a goal to find suitable pharmaceutical agents and methods to stimulate cell growth and/or reduce apoptosis for the treatment of various wasting diseases.

SUMMARY OF THE INVENTION

The present invention provides SERF2 as novel pharmaceutical agent for such treatments. In a first aspect, the present invention provides SERF2, a nucleic acid encoding said SERF2 or a cell expressing SERF2 for use as a medicament. In a related aspect the invention provides SERF2, a nucleic acid encoding said SERF2 or a cell expressing SERF2 for use in treating or preventing an atrophy disease or condition or for cell regenerative therapy or for increasing cellular growth in a patient.

Also provided is an in vivo or in vitro method of increasing the proliferation of stem cells or progenitor cells or reducing the rate of apoptosis of said cells, comprising administration of SERF2 or SERF2 encoding nucleic acids to said cells.

In a fourth aspect the invention provides a pharmaceutical composition comprising SERF2 or SERF2 encoding nucleic acids. Such a composition may comprise a pharmaceutically acceptable carrier or stabilizer.

As is apparent, all of these aspects are related to each other, are equivalent and all preferred embodiments relate to each one of these aspects equally. The subject matter of the present invention is further defined in the claims.

DETAILED DESCRIPTION

SERF2 (Small EDRK-rich factor 2) is a protein with a known sequence, see e.g. Swiss-Prot Database P84101 (human), P84102 (mouse) or NCBI Database NP_001018118 (human protein), NP_035484 (mouse protein), NM_001018108 (human nucleotide), NM_011354

(mouse nucleotide). Isoforms are deposited under database accession numbers NP_001018118.1, NP_001186804.1, NP_001186805.1, NP_001186806.1 and NP_001186807.1. In the past, it has also been referred to as H4F5rel (H4F5 related-SERF2 shares 69% sequence identity with H4F5, Scharf et al. nature genetics 20, 1998: 83-86). SERF2 is further disclosed in US 2007/042392 A1 (as SEQ ID NO: 1143, EBI database acc. No. AGI32189) and in WO 2000/55351 A1 (as SEQ ID NO: 1054, EBI database acc. No. AAB53514), both incorporated herein by reference. SERF2 is further disclosed in Van Ham Tjakko J et al., Cell, Vol. 142, No. 4 (2010), 601-612 and NCBI database acc no. AAC63516).

In the past, there have been different results on the functional capabilities of SERF homologue proteins. Some papers report a toxic role through aggregation of amyloidogenic proteins (e.g. van Ham et al. Cell 142, 2010: 601-612) while other reports describe a protective role via deposition of toxic proteins in inclusion bodies. It is important to appreciate that fibrillar aggregates of aggregation-prone proteins as described by van Ham et al. are a hallmark of neurodegenerative disorders only.

Several neurodegenerative diseases are associated with an expanded trinucleotide sequence CAG in genes. Since CAG codes for the amino acid glutamine, these disorders are collectively known as polyglutamine diseases. Although the genes (and proteins) involved in different polyglutamine diseases have little in common, the disorders they cause follow a strikingly similar course: If the length of the expansion exceeds a critical value of 35-40, the greater the number of glutamine repeats in a protein, the earlier the onset of disease and the more severe the symptoms. This fact suggests that abnormally long glutamine tracts render their host protein toxic to nerve cells, and all polyglutamine diseases are hypothesized to progress via common molecular mechanisms. One possible mechanism of cell death is that the abnormally long sequence of glutamines acquires a shape that prevents the host protein from folding into its proper shape. Polyglutamine (polyQ) diseases are classified as conformational neurodegenerative diseases, like Alzheimer and Parkinson diseases, and they are caused by proteins with an abnormally expanded polyQ stretch.

Using computer models of polyglutamine, it was shown that if, and only if, the length of polyglutamine repeats is longer than the critical value found in disease, it acquires a specific shape called a β-helix. The longer the glutamine tract length, the higher the propensity to form β-helices. Expansion of polyglutamine (polyQ) tracts in proteins results in protein aggregation and is associated with cell death in neurodegenerative diseases. Disease age of onset is correlated with the polyQ insert length above a critical value of 35-40 glutamines. The aggregation kinetics of isolated polyQ peptides in vitro also shows a similar critical-length dependence. By using computer simulations of isolated polyQ peptides, it was shown that a mechanism of aggregation is the conformational transition in a single polyQ peptide chain from random coil to a parallel β-helix. This transition occurs selectively in peptides longer than 37 glutamines. The production of the apparent toxic species—soluble oligomers—and their subsequent ability to cause neuronal injury depends on the precision of an intramembranous proteolytic cleavage. Some oligomeric species are small and soluble enough to diffuse readily through the brain parenchyma and affect synaptic structure and function and, ultimately, neuronal survival.

In a series of experiments, van Ham et al. (supra) tried to identify modifier of aggregation (MOAG-4/SERF as a regulator of age-related proteotoxicity in *C. elegans*. The authors found that depending on the number of glutamine residues (<40 residues), protein aggregation can be detected and is reduced when they introduced a point mutation in MOAG-4. However, life span was not influenced in these animals. The members of the SERF protein family seem to have similar functions as MOAG-4. In addition, overexpression of SERF1/2 increased aggregation of mutant Huntington protein and cell death in mouse fibroblasts.

Despite these interesting findings, the results of this paper evoke a number of questions:
1. Functional Studies in *C. elegans* often do not reflect the situation in humans or mammals, for instance recent results reveal a higher degree of species specificity among TCF proteins for coactivator interactions than for corepressor interactions, and uncover a basic difference between *C. elegans* and human TCF4 steady state nuclear levels. Another example is the dramatic difference between *C. elegans* and *D. melanogaster* unc-76 mutants on the one hand, which causes serious defects in the nervous system, and the mouse FEZ1 −/− knockout mice on the other, which show no morphological and no strong behavioural phenotype.
2. There are reports in literature which describe a protective role for the SERF protein family rather than a toxic one.
3. There is a marked difference in the AA-sequence between MOAG4 and SERF proteins (~50%), therefore functional differences might be due to protein sequence differences.
4. Most importantly, a highly artificial system is used. Only in cells transfected with 74 polyQ repeats, a situation that is never achieved in nature, aggregation takes place. In addition, aggregation is only seen with amyloidogenic proteins. Therefore, it remains to be seen if there is any natural function of MOAG4/SERF in the absence of exogenous proteins.

Nevertheless, in certain embodiments of the present invention the disease or condition to be treated is not one or more diseases or conditions selected from the groups of Alzheimer's disease, Parkinson's disease, Huntington's disease, or any polyglutamine diseases or any disease or condition caused by aggregation of amyloid fibers or of amyloidogenic proteins. In particular embodiments the disease or condition is not a disease or condition of the nervous system.

The results herein evidently show a protective and growth-supporting role of SERF2 in a variety of mammalian cell types. In several experiments it has been shown, that SERF2 induces proliferation in a variety of human cell lines. Beside cells of mesenchymal origin it also has effects on cells of the hematopoietic lineage and muscle cells, among others.

SERF2, as used herein relates to any SERF2 isoform or variant. In preferred embodiments SERF2 comprises or consists of an amino acid sequence as set forth in SEQ ID NO: 1, or an amino acid sequence that has at least 70% sequence identity with the sequence as set forth in SEQ ID NO: 1.

The term "sequence identity" refers to identity between two sequences, usually amino acid sequences, which can be determined by sequence alignment programs like BLAST, PSI-BLAST (www.ncbi.nlm.nih.gov/blast/) or ClustalW (www.ebi.ac.uk/clustalw/). These algorithms calculate the best match for the selected sequences, and line them up so that the identities, similarities and differences can be seen. The sequence identity to SEQ ID NO:1 is calculated to the entire sequence of SEQ ID NO: 1.

In preferred embodiments of the present invention the inventive SERF2 comprises or consists of a sequence with at least 70%, more preferred at least 75%, at least 80%, at least 85%, at least 90%, at least 95%, at least 98% or even 100%, sequence identity with the sequence as set forth in SEQ ID NO: 1.

SERF2 can be a recombinant SERF2. Further preferred it is of the same origin as the patient but also SERF2 variants from other animals can be used. Preferably the patient is a mammal, especially a human or non-human animal, in particular a domestic animal, such as pig, rodents, or a primate. Preferably the SERF2 is human SERF2 or SERF2 from a non-human animal, in particular a domestic animal, such as pig, rodents, or a primate.

As used herein "comprising" is used in an open meaning, i.e. that the SERF2 of the present invention may have further amino acids or protein components. It may be a fusion protein. Such extended SERF2 proteins may have in preferred embodiments a limited size, e.g. up to 2000 amino acids, up to 1800 amino acids, up to 1600 amino acids, up to 1400 amino acids, up to 1200 amino acids, up to 1000 amino acids, up to 800 amino acids, up to 600 amino acids, up to 400 amino acids, up to 300 amino acids, up to 200 amino acids, or up to 160 amino acids. Of course the invention also relates to SERF2 proteins that consist of any one of said sequences comprised in the above mentioned embodiments. "Consisting" is used in a closed and sequence limiting meaning.

Alternatively (or in combination) to using SERF2 proteins it is also possible to use nucleic acids that encode the above mentioned SERF2 protein and its variants. Such a sequence is e.g. set forth in SEQ ID NO: 2, which encodes SEQ ID NO: 1.

Nucleic acids can be used to induce production of SERF2 in cells. Preferred formulations for nucleic acid delivery are e.g. liposomes, microemulsions, micelles or vesicles for controlled delivery. The cell may then produce and secrete SERF2 to provide a continuous production of the therapeutic agent.

Also provided is a cell that expresses SERF2 for the inventive uses. Such a cell preferably continuously secretes SERF2 to provide for the therapeutic effect. Such a cell can be any cell. In preferred embodiments the cell is not-immunogenic to the patient, e.g. it is a cell obtained from the patient that has been genetically engineered to recombinantly express SERF2. This modification of the cell can be performed in vitro or in vivo.

The previous and further detailed description relates to the SERF2 protein, the nucleic acid and the cells equally, in particular since the directly active therapeutic agent of the nucleic acid or the cell is also the expressed SERF2. All three embodiments are conterminously referred to as "SERF2" herein, wherein SERF2 protein is preferred since it is the directly acting agent.

The present invention provides in particular SERF2 for use in treating or preventing an atrophy disease or condition or for cell regenerative therapy.

"Preventing" as used herein does not require an absolute prevention in that a patient will never develop the diseases or conditions but it relates to a reduced risk in developing the disease or condition. It is a prophylactic treatment. Other forms of treatment occur after onset of the disease or condition, e.g. when a patient in need of a therapy has been identified. "Treating" does not mean that a disease or condition is completely cured. It may also refer to an improvement or amelioration of symptoms.

Atrophy is the general physiological process of reabsorption and breakdown of tissues, involving apoptosis on a cellular level. It is also termed as a partial loss of a part of the body. It can be caused by diseases or it can be a part of normal body development, such as during aging. In special embodiments, the atrophy is muscle atrophy, but other tissues may be affected and treated according to the invention as well. SERF2 achieves downregulation of myonuclear apoptosis, effective in maintaining muscle mass and function in late life and additionally stimulates cellular proliferation and development.

It essentially shifts the equilibrium between apoptosis and proliferation towards proliferation an regeneration. SERF2 decreases apoptosis and increases proliferation. Thus it can be used to treat cells or diseases with increased apoptosis and/or reduced proliferation or regeneration of cells. Thus in a preferred embodiment the atrophy treated according to the invention is associated with an increased apoptosis or reduced regeneration of cells. An atrophy might be a reduction of the mass of a certain tissue. Such a tissue can be a muscle (e.g. in sarcopenia), the skin (e.g. in medication- or age-caused skin thinning), a bone or an internal organ such as the liver, a tissue of the hematopoietic system, e.g. bone marrow, spleen, tonsils, lymph nodes.

In addition to treating atrophies, the invention can be used to increase cellular mass even when there is no shortcoming of a specific cell type. It can be used as a time-limited or extended therapy to increase a certain tissue mass. Such a tissue can e.g. be a muscle (e.g. for body building), the skin, a bone or an internal organ, such as the liver and tissues of the hematopoietic system, e.g. as mentioned above.

In preferred embodiments the treated atrophy is a reduction of cells selected from the group of muscle cells, in particular heart muscle cells or skeletal muscle cells or smooth muscle cells, a connective tissue cell, in particular a cell of connective tissue surrounding a muscle or a bone cell, epithelial cells, in particular blood vessel cells, and satellite cells, or bone cells (e.g. osteoblasts or osteoclasts).

The disease or condition to be treated or prevented can in special embodiments be selected from sarcopenia, cachexia, dystrophy, especially muscular dystrophy, hypoplasia, hypotonia, especially hypotonia after an operation, polymyositis, fibromyalgia, myotubular myopathy, metabolic diseases of the muscular system, Parkinson's, myasthenia gravis, cardiomyopathy, cardiomyocyte contractile dysfunction, skin aging. The inventive therapy can be for preventing muscle loss or muscle dystrophy after a time in a surgical cast or any other immobility, or any combination thereof. The disease or condition to be treated can be associated with insufficient angiogenesis. Diseases associated with insufficient angiogenesis are characterized by a loss in blood circulation and insufficient oxygen supply to a particular tissue (in particular the one of the tissues mentioned above to be treated in preferred embodiments). Diseases with insufficient angiogenesis are e.g. ischemic heart disease and conditions resulting due to anti-angiogenetic treatments, e.g. in therapies with antibodies that reduce or prevent blood vessel formation, e.g. in a therapy of macular degeneration, or in a therapy of cancer. A further disease or condition to be treated can be neutropenia, especially chemotherapy-induced neutropenia, which can be treated according to the invention by increasing proliferation or reducing apoptosis of cells of the hematopoietic system. Preferably hematopoietic stem cells are expanded in vivo or ex vivo and used to ameliorate symptoms in cancer treatments that would result in a reduction of blood cells. Of course also other stem cells, e.g. of any one of the tissues mentioned above, can be expanded using SERF2 according to the invention.

Somatic cells have both a limited lifetime and regeneration ability, which is especially evident during aging. Sarcopenia is defined as the degenerative loss of skeletal muscle and muscle strength in elderly people. Muscle loss causes a major disability of the elderly in everyday life, and leads to an enormous increase of healthcare cost. The risk of fall and fractures is enhanced and a loss of independence and live quality is evident. The reasons for the muscle loss are among others, proteolysis, lack of protein synthesis and muscle fat content. A mechanism for the loss of muscle cell mass is the decrease of satellite cells in skeletal muscle. Satellite cells are specialized cells located in the basal membrane of muscles and are crucial for muscle regeneration and growth of muscle tissue. The number of satellite cells decreases during age and is a reason for sarcopenia.

For the reason mentioned in the background section, new therapies to prevent apoptosis in muscle cells and to induce the formation of new muscle tissue are in great demand for treating sarcopenia and other diseases associated with cell loss.

In addition to the beneficial effects of SERF2 for muscle and satellite cells, it could be used for a variety of other cell types. The effect of SERF2 on hematopoietic cells (HC) is of utmost importance. It does protect these cell types from GF-deprived cell death and leads to prolonged survival. This is especially important in diseases where only small numbers of absolutely necessary cells are left (for instance during chemotherapy) or if rare cell types such as stem cells need to be expanded. Related to these effects, SERF2 can be used in vivo or in vitro to increase hematopoiesis or blood cell amounts, e.g. blood cell concentrations, in a subject. This may be of therapeutic or non-therapeutic use. Thus the present invention also relates to therapies to treat a blood cell deficiency or a subject in need of blood cell increase. The blood cells may be selected from erythrocytes (red blood cells), PBMCs, white blood cells, T cells, granulocytes and macrophages or monocytes.

Given the new results presented herein, that SERF2 exerts a proliferative and life-span enhancing effect on epithelial cells, SERF2 is well suited as a drug to prevent skin aging. Due to its relatively low molecular weight it could be packaged into liposomes and used as an efficient additive in medical care cosmetics. Thus SERF2 can also be used for cosmetic or therapeutic uses in the treatment of skin, to prevent or reduce aging effects.

Action of epithelial cells is particularly visible during angiogenesis. As shown herein, angiogenesis can be stimulated in vivo or in vitro by administering SERF2. Thus the present invention also provides for the use of SERF2 for stimulating angiogenesis. A patient with tissues with insufficient artery supply may be treated. The patient may have anoxic tissues that are treated by the present invention. The tissue with insufficient artery supply may also be acute or chronic, e.g. be in this state for at least 14 days, preferably at least 18 days, especially preferred at least 22 days, even more preferred at least 28 days, for at least 34 days, at least 40 days, at least 50 days or even at least 60 days. Thus, the present invention relates to a treatment of a patient who is in need of an induction of angiogenesis with SERF2, in particular in the tissue in need of such therapy. Preferably the therapy is topical.

SERF2 can be administered to a patient, e.g. the SERF2 protein or nucleic acid is administered directly by an adequate means to the patient's system or specific tissue.

Alternatively, cells of a patient are treated ex vivo with SERF2 and said cells are administered to said patient. SERF2 treated cells are activated for proliferation and can perform the necessary regenerative functions in vivo. The readministered administration is preferably topical, in particular to the tissue of origin of the cell (e.g. reapplying a muscle cell/muscular stem or progenitor cell such as satellite cells to a muscle). Preferred cells to be treated ex vivo and readministered is any kind of stem cell or progenitor cell, which generally have enhanced potential for proliferation and tissue regeneration.

The disease or condition to be treated according to the invention may be chronic or acute. "Chronic" in preferred embodiments relates to a disease or condition that exist for at least 14 days, preferably at least 18 days, especially preferred at least 22 days, even more preferred at least 28 days, within at least 34 days, at least 40 days, at least 50 days or even at least 60 days.

The present invention further relates to an in vitro or in vivo method of increasing the proliferation of stem cells, progenitor cells, epithelial cells, in particular epidermal skin cells, mesenchymal cells, in particular cardiomyocytes, satellite cells, skeletal muscle cells, hematopoietic cells, in particular hematopoietic stem cells or progenitor cells, or reducing the rate of apoptosis of said cells, comprising administration of SERF2 or SERF2 encoding nucleic acids to said cells. Hematopoietic cells may e.g. be cells or stem or progenitor cells of the bone marrow, spleen, tonsils or lymph nodes. Such an in vivo method can be suitable for one of the above mentioned therapies. In vitro methods can be used to proliferate cell cultures or in an ex vivo step for proliferating cells, which may then be reinserted into a patient in the course of a therapy.

Such cells are preferably selected from the group of muscle cells, in particular heart muscle cells or skeletal muscle cells or smooth muscle cells, a connective tissue cell, in particular a cell of connective tissue surrounding a muscle, and stem cells, progenitor cells, in particular satellite cells, hematopoietic cells, skeletal muscle cells, epithelial cells, in particular epidermal skin cells. The inventive SERF2 can be used to increase the mass of these cells in any tissue, e.g. to increase heart mass or volume. This increase can be used to treat a disease with an insufficiency of such cells, e.g. a muscle weakness, especially a hear muscle weakness, or for anabolic reasons. A particular preferred embodiment relates to the in vitro preparation of skin cells for an artificial skin, which cells or skin can be used in skin repair.

SERF2 (as always including proteins, nucleic acids or cells) can be administered in any way known in the art. Especially preferred forms of administration are topical administrations. Preferred topical administrations means are transdermal patches or by minipumps, which can continuously provide SERF2 on the site or tissue of need thereof. Of course, also a systemic administration is possible, to provide overall increased proliferative activity. In case of systemic administration—but also for topical forms of administration—SERF2 can be linked, e.g. fused, to a tissue homing molecule, such as a ligand of a surface receptor, specific for a selected kind of tissue. Such tissues can be selected from the above, e.g. muscle (heart, skeletal or smooth) cells, endothelial cells etc. Such a homing molecule allows tissue specific action of SERF2 with any kind of administration.

In preferred embodiments the administered SERF2 concentration is from 0.5 µg/ml to 1000 µg/ml, preferably 1 µg/ml to 800 µg/ml, especially preferred 2.5 µg/ml to 500 µg/ml, even more preferred 4 µg/ml to 300 µg/ml, most preferred 5 μg/ml to 100 μg/ml. These ranges have proved to be especially effective in the inventive therapy.

As shown in the examples, SERF2 can increase proliferation and/or reduce apoptosis of cells under stress, e.g. oxidative stress. Thus in a preferred embodiment the cells treated according to the invention are suffering from stress, in particular oxidative stress such as stress induced by reactive oxygen species including .OH.

The invention further relates to a pharmaceutical composition comprising SERF2 proteins or SERF2 encoding nucleic acids or the SERF2 expressing cells (all three embodiments conterminously referred to as "SERF2", preferably SERF2 protein). Pharmaceutical compositions or formulations for therapeutic use may comprise a pharmaceutically acceptable diluent, carrier, solubilizer, emulsifier, preservative, stabilizer and/or adjuvant. The invention also provides for pharmaceutical compositions comprising a therapeutically effective amount of SERF2. The term "therapeutically effective amount" means an amount which provides a therapeutic effect for a specified condition and route of administration. The composition may be in a liquid or lyophilized form and comprises a diluent (Tris, acetate or phosphate buffers, NaCl) having various pH values and ionic strengths, solubilizer such as Tween or Polysorbate, carriers such as human serum albumin or gelatin, preservatives such as thimerosal or benzyl alcohol. Selection of a particular composition will depend upon a number of factors, including the condition being treated, the route of administration and the pharmacokinetic parameters desired.

Preferred formulations are formulations for topical administration. Especially preferred is a hydrogel, a patch, in particular a transdermal patch and a surgically inserted delivery means, such as a minipump. Also encompassed are compositions comprising SERF2 modified with water soluble polymers to increase solubility, stability, plasma half-life and bioavailability. Compositions may also comprise incorporation of SERF2 into liposomes, microemulsions, micelles, microparticles or vesicles for controlled delivery over an extended period of time.

In special embodiments SERF2 is provided with a carrier. The carrier is preferably selected from a gel, preferably a hydrogel, or a wound dressing or a swab, optionally impregnated with a solution containing SERF2. Further carriers comprise carriers for slow-release which release the active agent combination as a longer effective application delayed or slower. Such a preparation with a corresponding carrier is especially suitable for topical and quick administration.

In particular, the present invention provides the pharmaceutical composition for use as a medicament, or for any one of the above described uses for SERF2.

The present invention will be further explained by the following figures and examples without being limited to theses specific aspects of the invention.

FIGURES

FIG. 1: Analysis of SERF2 after the second purification step (HIC column). Equal amounts of fractions 1-9 were loaded onto an SDS gel and subjected to western blot analysis. SERF2 (arrow) appears at appr. 13 kDa and is not retarded on the HIC column whereas impurities are retained. The higher apparent molecular weight is due to large amounts of positive charges (19 residues), which alters elution behavior of SERF2.

Figure 2:
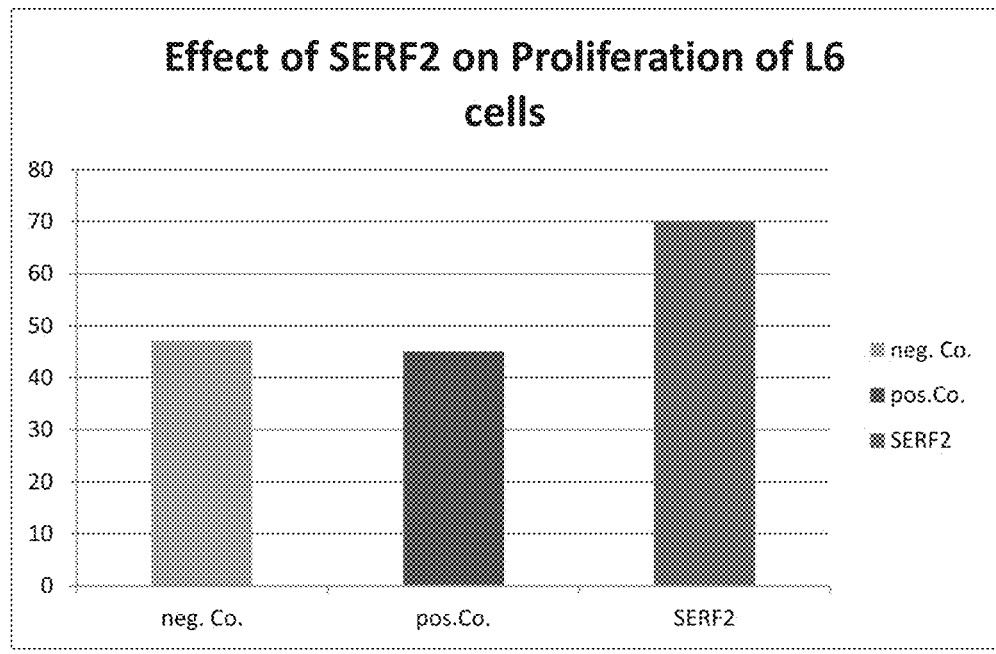

FIG. 2: Effect of SERF2 on Proliferation of rat skeletal muscle cells (L6). $1 \times 10^4$ L6 cells were seeded per well containing 100 μl growth medium. Cells were incubated over night at +37° C., 5% v/v $CO^2$ and humidified atmosphere. Prior performing the assay, viability of cells was checked under the microscope. Cells were washed three times with 100 μl DPBS per well. SERF2 was diluted μg/ml) in DMEM and 100 μl/well were added to the cells. Finally, cells were incubated at +37° C. for various time points. Subsequently 10 μl/well AlamarBlue™ reagent (Invitrogen) was added. Plates were incubated for one hour at +37° C. Fluorescence (Ex. 570 nm, Em. 585 nm) was measured using a Varioskan Flash multi-plate reader (Thermo Scientific). Obtained Data were evaluated using Microsoft Excel and Graph Pad Prism V4.

Figure 3:
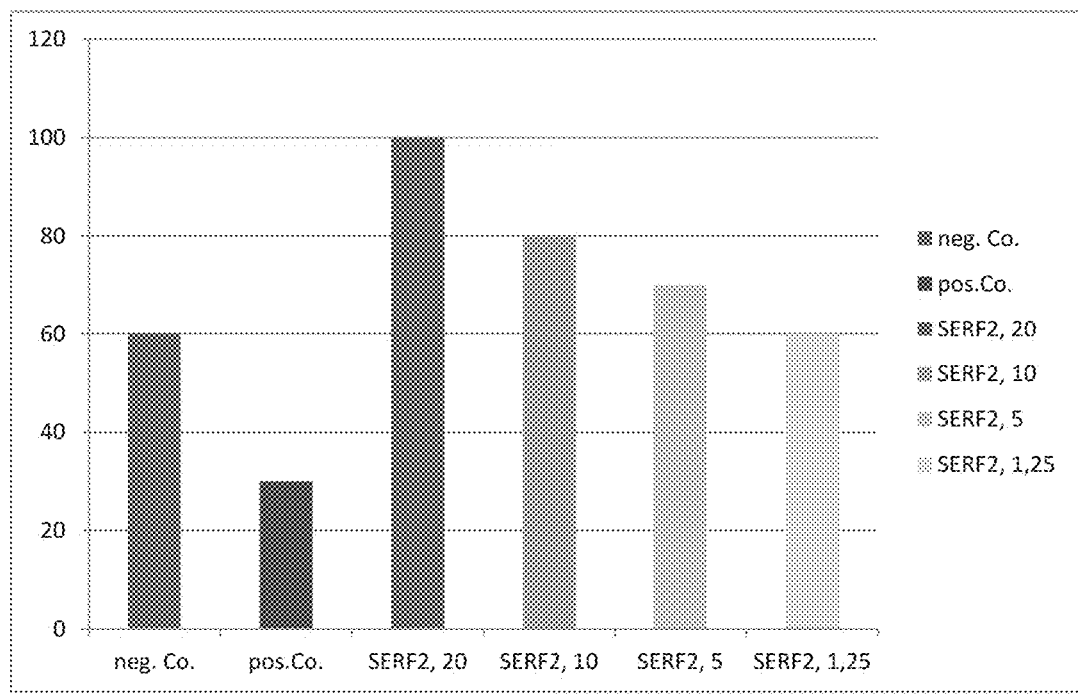

FIG. 3: Effect of SERF2 on Proliferation of H9c2 cells is dose-dependent. Proliferation assay was performed essentially as in FIG. 2. Incubation time was 24 hrs, added SERF2 concentrations ranged from 20 to 1.25 μg/ml.

Figure 4:
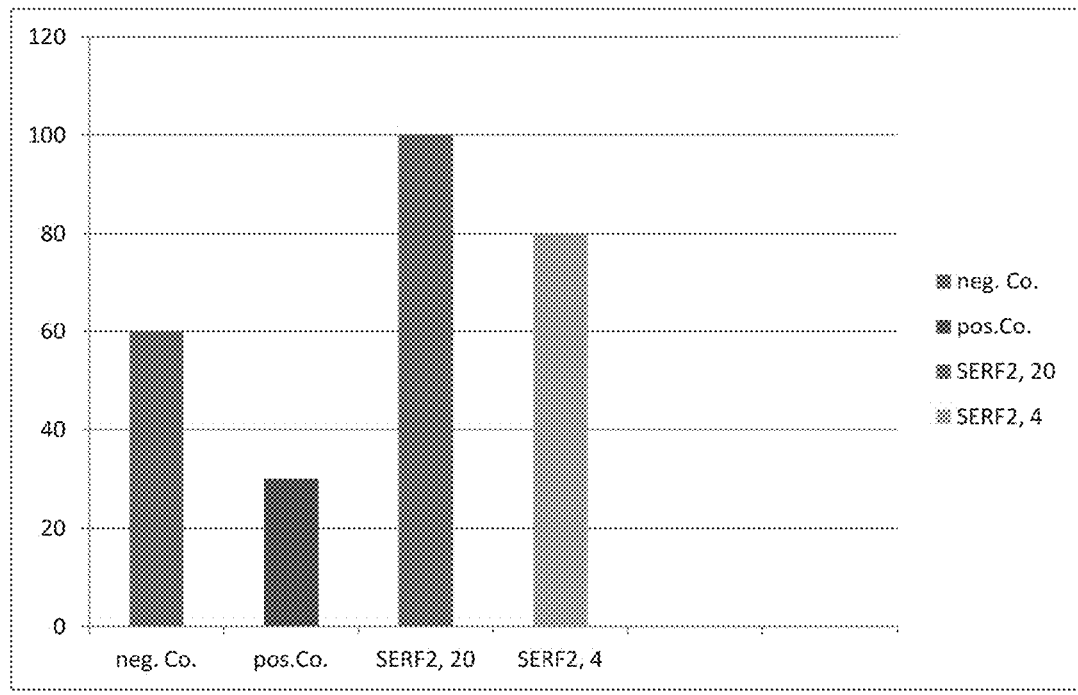

FIG. 4: Effect of SERF2 on Proliferation of mouse satellite cells (MuMa23/P13). Proliferation assay was performed essentially as in FIG. 2. Incubation time was 24 hrs, added SERF2 concentrations were 20 and 4 μg/ml, respectively.

Figure 5:
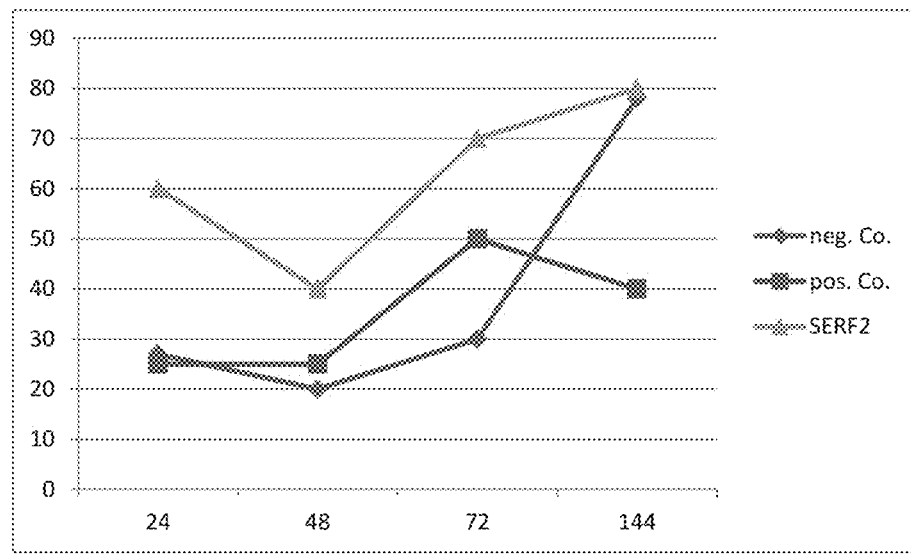

FIG. 5: Kinetics of the Effect of SERF2 on Proliferation of rat cardiomyocytes (H9c2). Cells stimulated with SERF2 (green line) responded with proliferation and reached max. proliferation rate after 6 days. Proliferation assay was performed essentially as in FIG. 2. Incubation times were 24, 48, 72 and 144 hrs, the SERF2 concentration added was 5 μg/ml.

Figure 6:
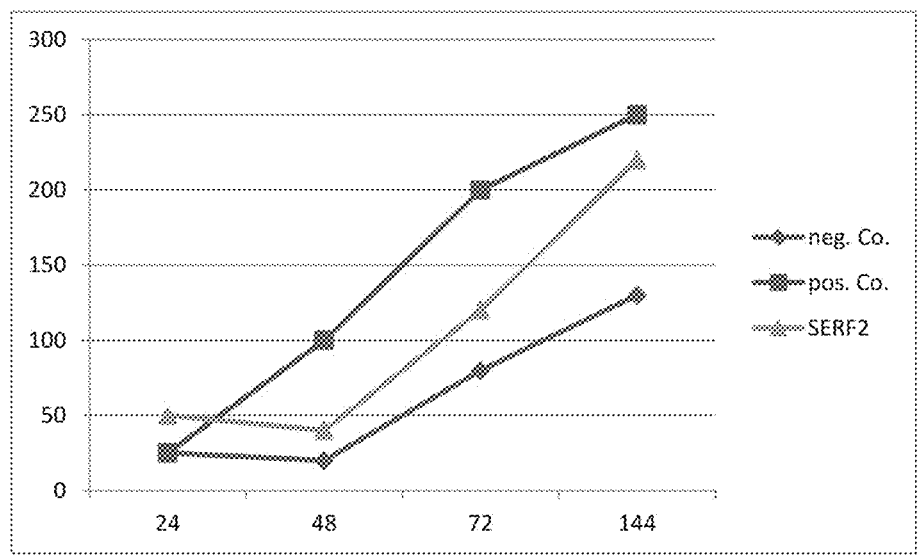

FIG. 6: Kinetics of the Effect of SERF2 on Proliferation of rat skeletal muscle cells (L6). Cells stimulated with SERF2 (green line) responded with proliferation and reached a max. proliferation rate after 6 days. Proliferation assay was performed essentially as in FIG. 2. Incubation times were 24, 48, 72 and 144 hrs, the SERF2 concentration added was 5 μg/ml.

Figure 7:
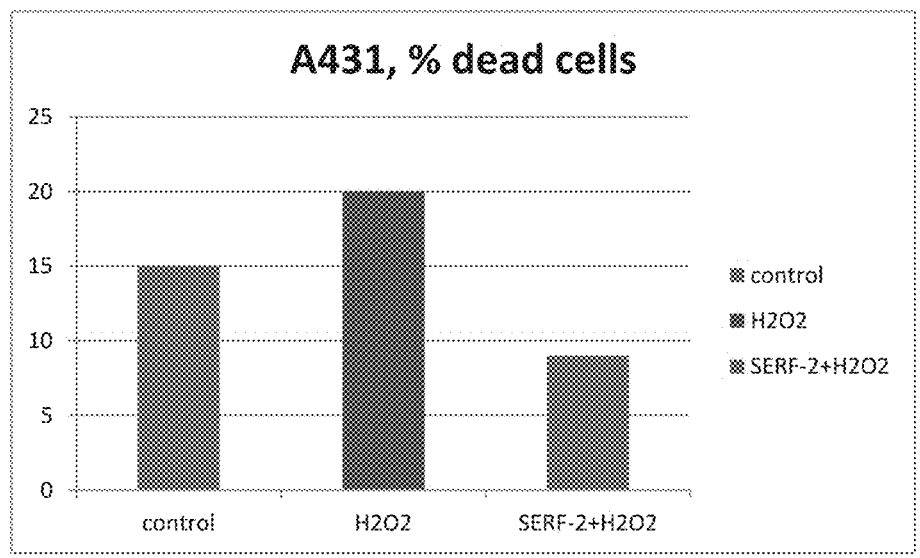

FIG. 7: SERF2 protects a human epithelial cell line (A431) from $H_2O_2$-induced apoptosis. Experiments were performed in 6-well plates containing 5 ml cell culture medium (serum-free) per well and were seeded at a cell density of $1*10^6$ cells/well and cultured overnight. On the next day 200 mM $H_2O_2$ or 200 mM $H_2O_2$ and SERF2 (5 μg/ml) was added to cultures. After 6 hours of incubation, the adherent cells were harvested, washed 3 times in PBS and dead cells were detected by trypan-blue staining using light microscopy. Shown is the percentage of dead cells.

Figure 8:
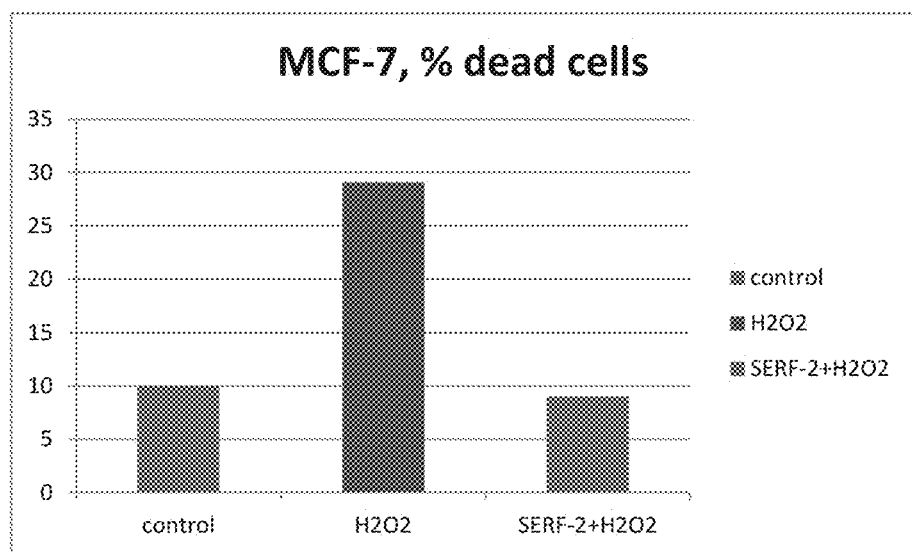

FIG. 8: SERF2 protects a human epithelial cell line (MCF-7) from $H_2O_2$-induced apoptosis. Experiments were performed in 6-well plates containing 5 ml cell culture medium (serum-free) per well and were seeded at a cell density of $1*10^6$ cells/well and cultured overnight. On the next day 200 mM $H_2O_2$ or 200 mM $H_2O_2$ and SERF2 (5 μg/ml) was added to cultures. After 6 hours of incubation, the adherent cells were harvested, washed 3 times in PBS and dead cells were detected by trypan-blue staining using light microscopy. Shown is the percentage of dead cells.

Figure 9:
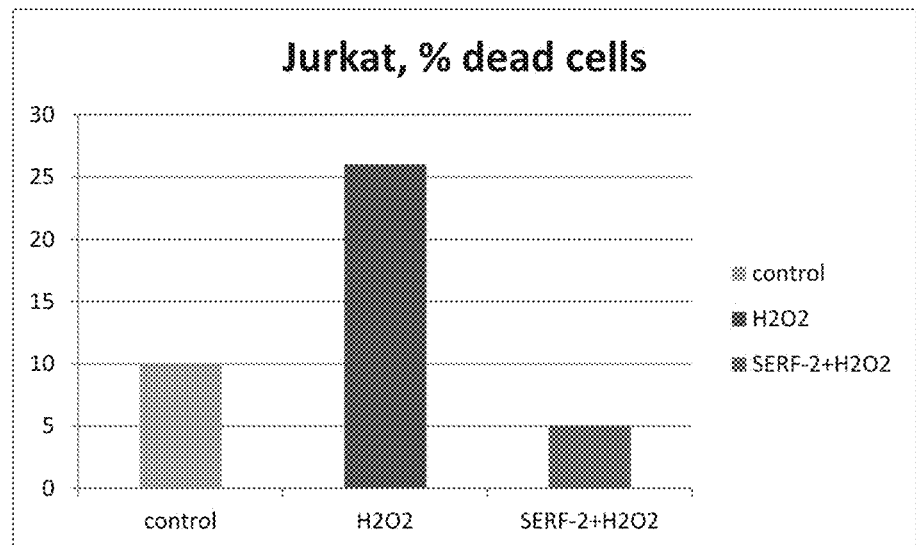

FIG. 9: SERF2 protects a human T-cell line (Jurkat) from H2O2-induced apoptosis. Experiments were performed in 6-well plates containing 5 ml cell culture medium (serum-free) per well and were seeded at a cell density of $1*10^6$ cells/well and cultured overnight. On the next day 200 mM $H_2O_2$ (red bar) or 200 mM $H_2O_2$ and SERF2 (green bar; 5 μg/ml) was added to cultures. After 6 hours of incubation, the adherent cells were harvested, washed 3 times in PBS and dead cells were detected by trypan-blue staining using light microscopy. Shown is the percentage of dead cells.

Figure 10:
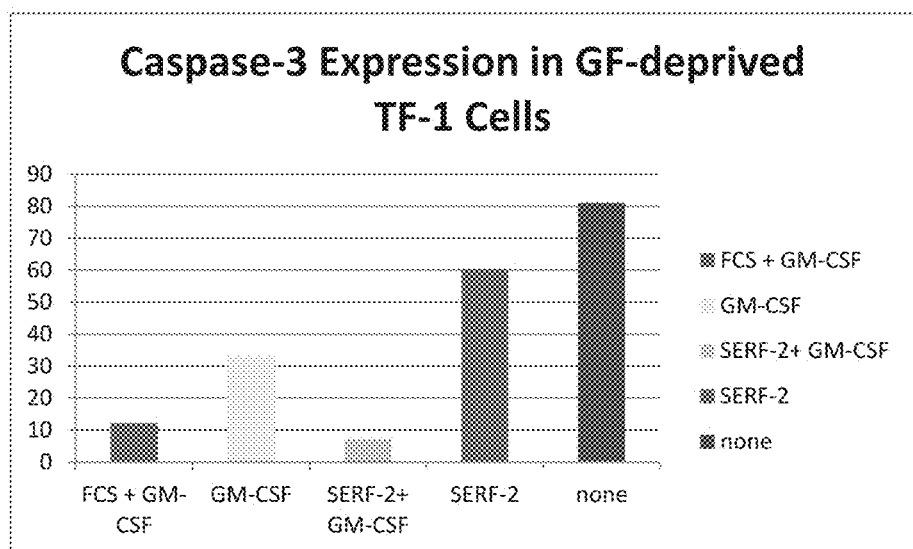

FIG. 10: SERF2 compensates for FCS and alleviates apoptosis in growth factor-dependent human myeloid cells.

Figure 11:
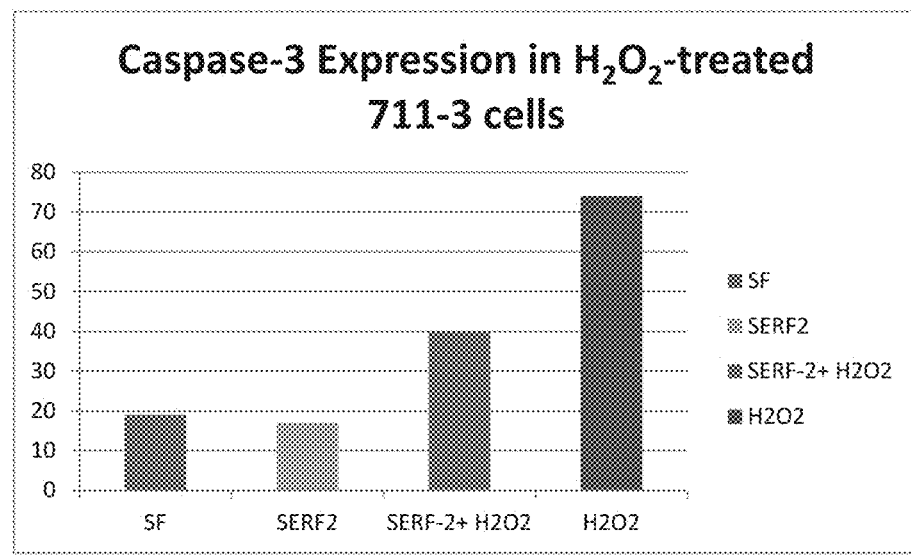

TF-1 cells were incubated under different culture conditions: FCS+GM-CSF (dark blue), serum-free medium+GM-CSF (5 μg/ml; pale blue), serum-free medium+GM-CSF+SERF2 (5 μg/ml; lime), serum-free medium+SERF2 (green) and serum-free medium only (red). After 9.5 hours culture supernatants were analyzed by an ELISA-technique for caspase-3 expression levels. Results are expressed as pNA in pmol/μl FIG. 11: SERF2 alleviates apoptosis in a human B cell line. 711-3 cells were incubated under different culture conditions: serum-free medium (dark blue), serum-free medium+SERF2 (5 μg/ml; lime) serum-free medium+SERF2+$H_2O_2$ (green) and serum-free medium+$H_2O_2$ (red). After 9.5 hours culture supernatants were analyzed by an ELISA-technique for caspase-3 expression levels. Results are expressed as pNA in pmol/μl.

Figure 12A:
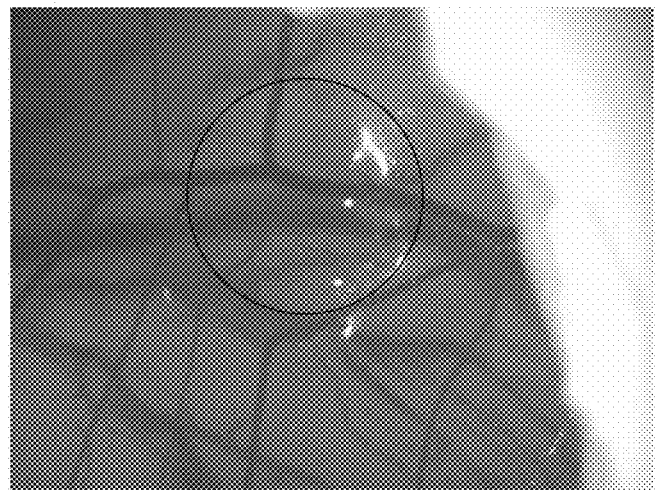
Figure 12B:
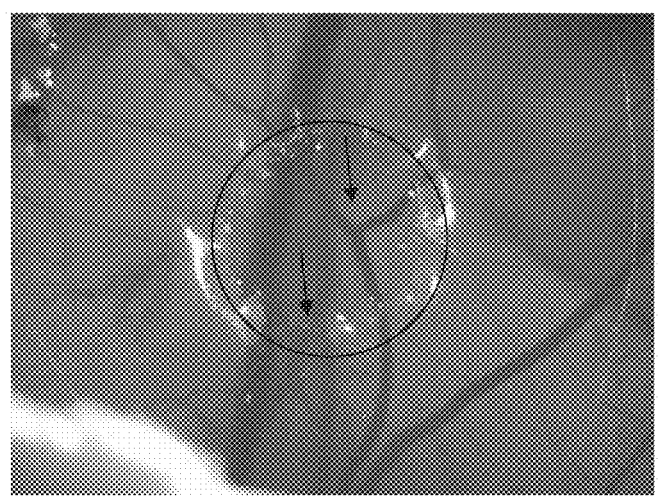
Figure 12C:
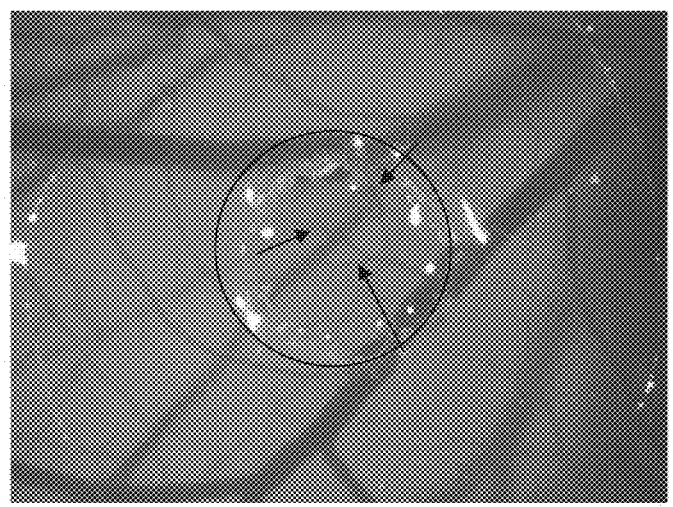

FIG. 12: Proangiogenic effect of SERF2 in CAM assays. To evaluate the pro-angiogenic properties of SERF2, 3 μg of A: PBS and C: SERF2 was applied per CAM. B: VEGF-A (0.5 μg/CAM) was used as positive control, PBS served as a negative control. New vessels were identified in VEGF and SERF2-treated CAMs. Treatment was performed on embryonic day 6 and 7. Angiogenic responses were evaluated microscopically. Pictures shown were taken for documentation on day 6.

Figure 13A:
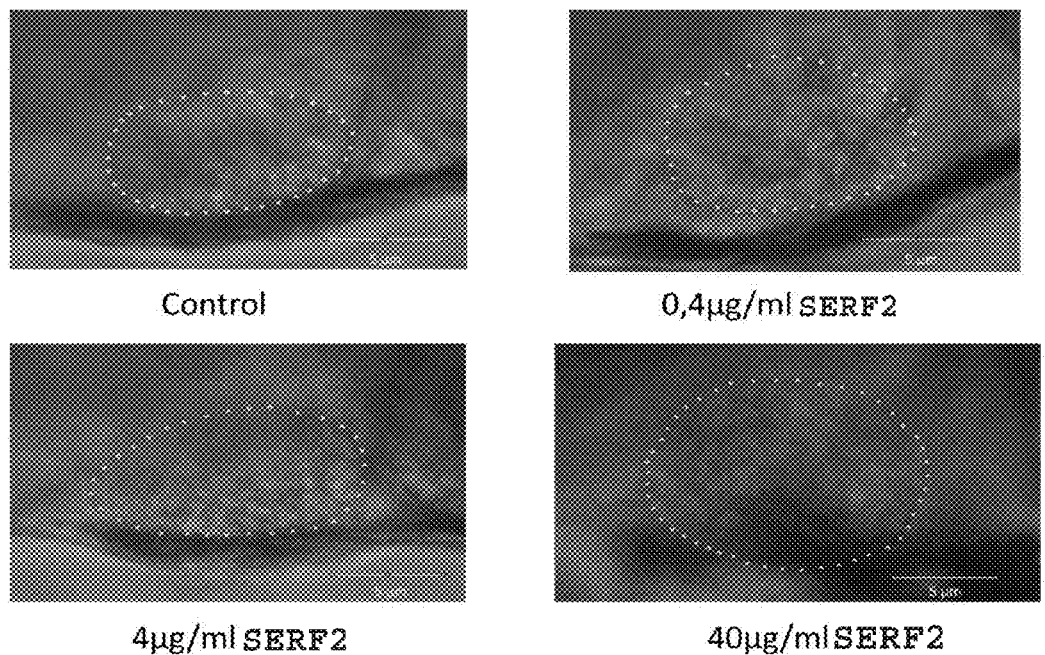
Figure 13B:
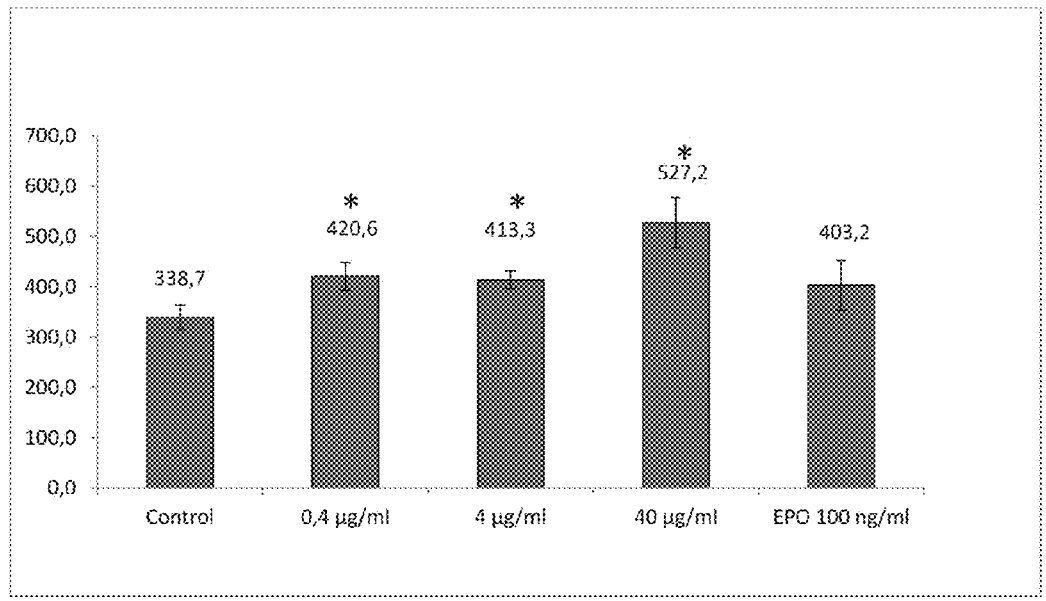

FIG. 13: a: Changes in heart size in 7 dpf old zebrafish incubated with different doses of SERF2. b: Changes in heart volume in 7 dpf old zebrafish incubated in different concentrations of SERF2 and erythropoietin (EPO). Significant differences to control animals are indicated by asterisks.

Figure 14:
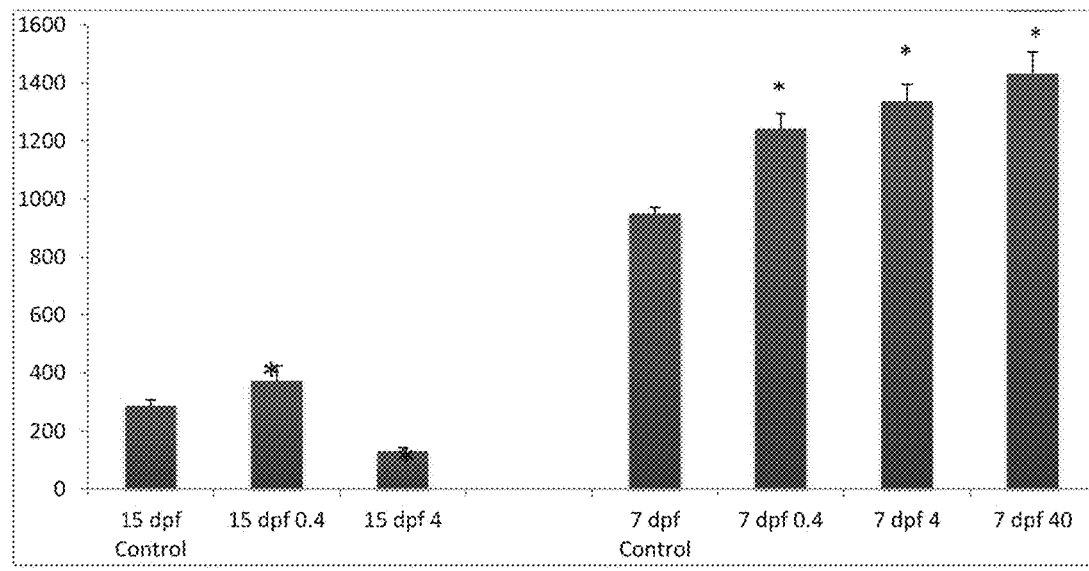

FIG. 14: Changes in blood cell concentrations in zebrafish incubated in different doses of SERF2. Shown are mean values (blood cells/nl) and SEM. Asterisks indicate significant differences to control animals.

Figure 15:
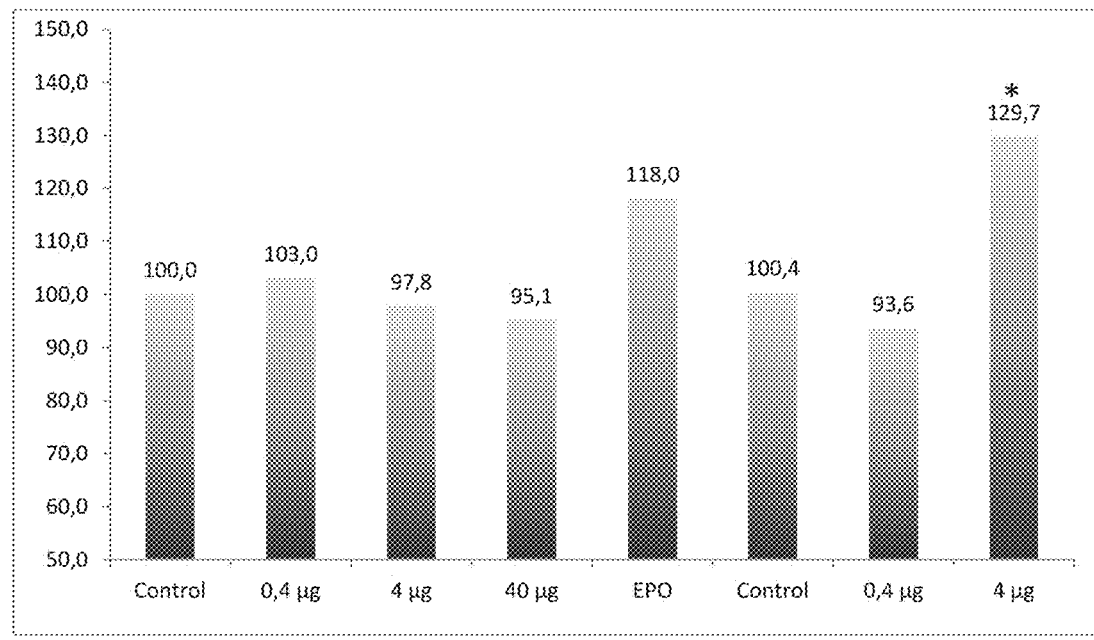

FIG. 15: Changes in proliferation of endothelial cells of the caudal fin in 7 dpf or 15 dpf old zebrafish induced by different doses of SERF2 or EPO. Asterisk indicates significant differences to control animals.

Figure 16:
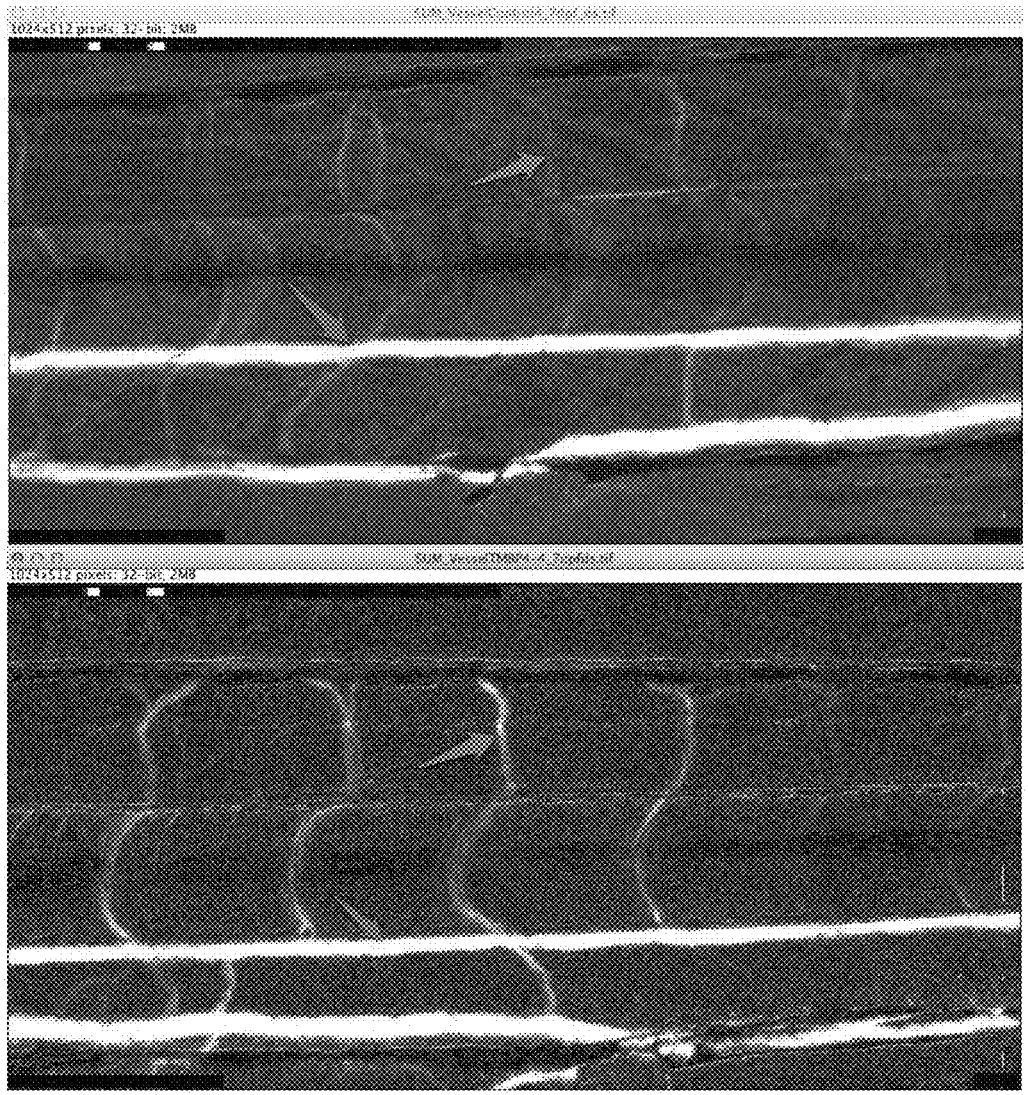

FIG. 16: Imaging of tail vasculature in 7 dpf zebrafish (top image=control, lower image=SERF2-treated). Magenta arrows indicate the dorsal artery, blue arrows the intersegmental vessels.

Figure 17:
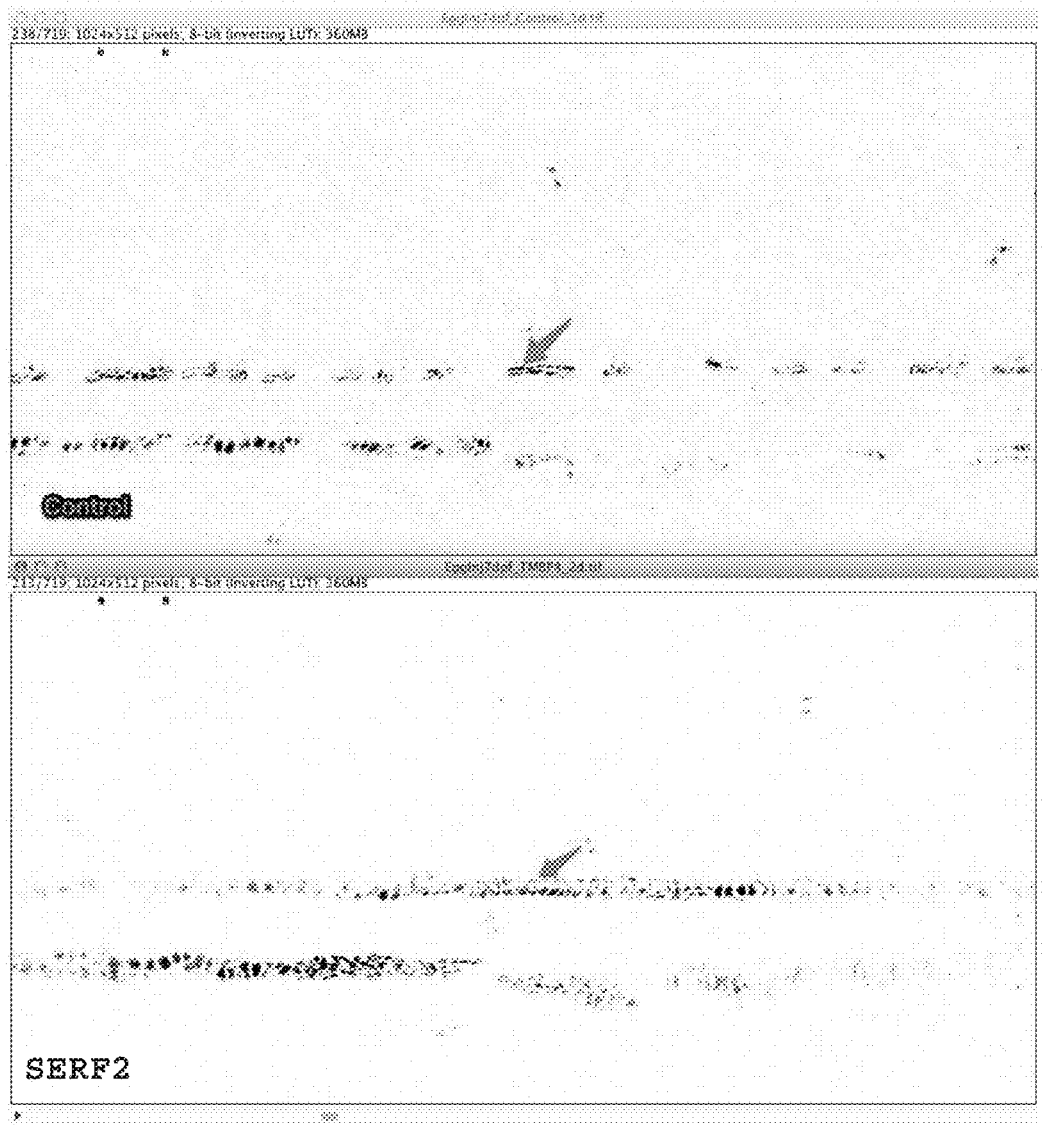

FIG. 17: Detection of blood cells (green arrows) in 7 dpf zebrafish (top image=control, lower image=SERF2-treated). To determine blood cell concentration the number of detected cells were divided by vessel volume.

Figure 18:
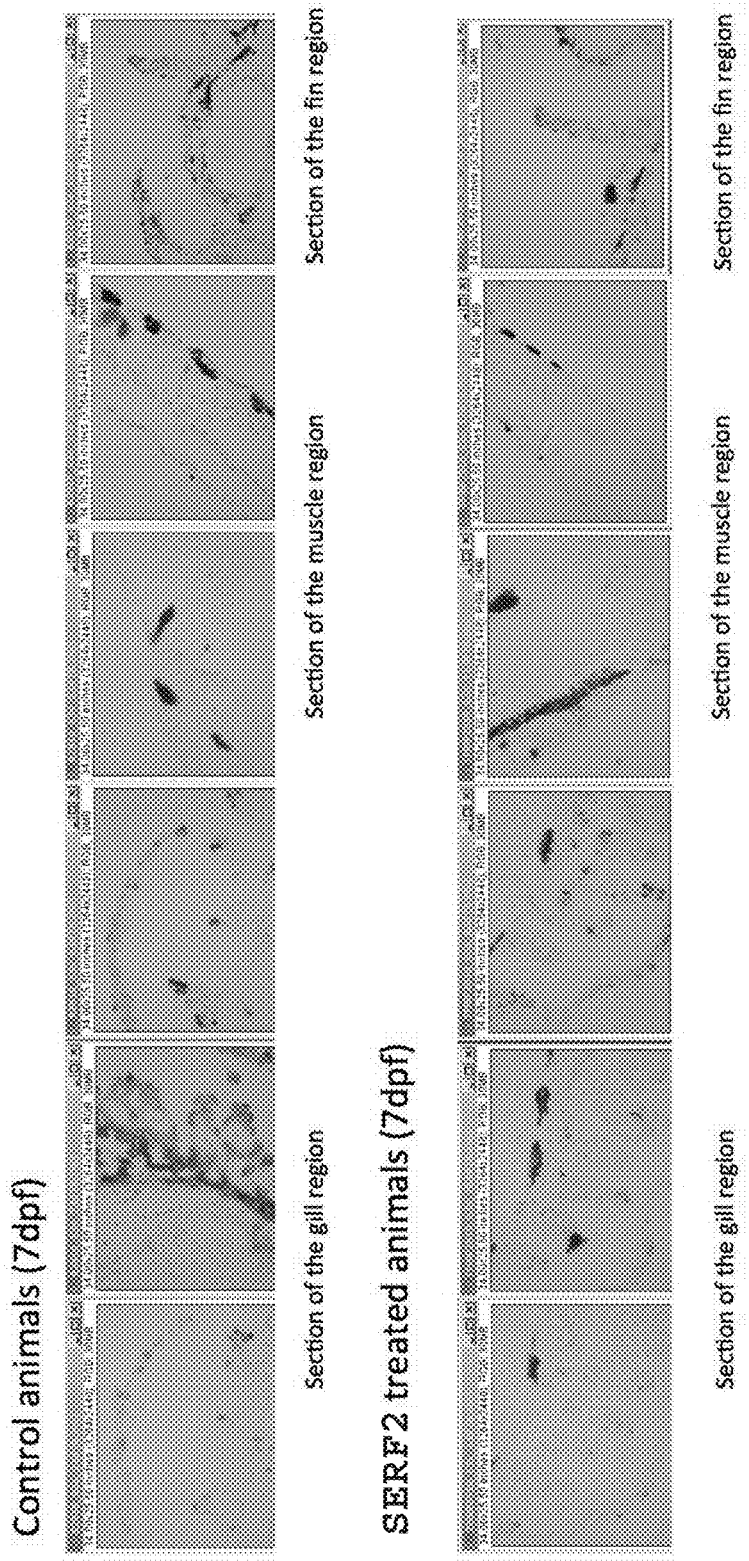

FIG. 18: Apoptotic cells detected by TUNEL technology in gill, skeletal muscle and tail sections. From these experiments it is evident that the number of specifically stained cells in SERF2-treated animals is lower in different regions as compared to untreated animals.

EXAMPLES

Example 1

Material & Methods 1.1 SERF2—Cloning, Expression and Purification

SERF2 was identified by colony hybridisation with a AB4 cDNA library. The coding sequence of SERF2 is 180 bp, the length of the mature protein is 59 amino acids, the molecular weight 6899, the pI 10.44.

```
SEQ ID NO 2:  atgacccgcggtaaccagcgtgagctcgcccgccagaagaatatgaaaaag

SEQ ID NO 1:  M  T  R  G  N  Q  R  E  L  A  R  Q  K  N  M  K  K cagagcgactcggttaagggaaagcgccgagatgacgggctttctgctgccgcccgcaagcag
 Q  S  D  S  V  K  G  K  R  R  D  D  G  L  S  A  A  A  R  K  Q agggactcggagatcatgcagcagaagcagaaaaaggcaaacgagaagaaggaggaacccaag
 R  D  S  E  I  M  Q  Q  K  Q  K  K  A  N  E  K  K  E  E  P  K tag
-
```

SERF2 was cloned codon-optimized into pET28 vector (inferring Kanamycin resistance) at 5'NcoI and 3'XhoI site without tags. SERF2 was expressed in BL21 E. coli.

An overnight pre-culture was prepared from a glycerol stock in selective M9ZB Medium and incubated at 37° C., shaking at 220 rpm. The next day, the overnight pre-culture was diluted to $OD_{600}$=0.1 and incubated at 37° C., shaking at 220 rpm until $OD_{600}$=0.5. Subsequently, protein expression was induced with IPTG at a final concentration of 1 mM. The culture was then incubated for 4 hrs at 30° C., followed by an overnight incubation at room temperature, shaking at 220 rpm. Bacteria were harvested by centrifugation for 2 h at 2500 g.

1.2 Purification of SERF2

For disruption, cells were resuspended in lysis buffer [75 ml/l culture volume; 50 mM Na-phosphate pH 8, 300 mM NaCl, 0.2% Triton X-100] and subjected to three freeze/thaw cycles at −80° C. After the third thawing, 30 μg/l DNAseI was added, and the lyzed cells were incubated at 37° C. for 30 minutes. Supernatant was collected by centrifugation for 2 hours at 2500 g.

For purification, the filtered lysate (0.22 μm) was loaded onto a SP-Sepharose column (70 ml CV) in 20 mM Tris pH8.0 at a flow rate of 14 ml/min. Fractions were eluted by a linear gradient with 20 mM Tris/1M NaCl pH 8.0 recording protein at 214 nm. After isolating relevant fractions via silver stained SDS PAGE gel and western blotting, respectively, ammonium sulphate was slowly added to a final saturation of 30% stirred overnight. Subsequently, the salt-enriched SERF2 was ultrafiltered (0.22 μm) and subjected to a second purification via a Hi Trap Octyl-Sepharose FF column (25 ml CV) at a flow rate of 7 ml/min. Relevant fractions were identified via silver stain stained SDS PAGE gel and western blotting (FIG. 1), pooled and dialysed against 20 mM Na-phosphate pH 7.4.

1.3 Cell Culture

Rat derived embryonic cardiomyocytes H9c2 (ATTC CRL-1446) and embryonic skeletal muscle cells L6 (ATTC CRL-1458) were cultured in Dulbecco's Modified Eagle Medium high glucose (DMEM, Sigma Aldrich) containing 10% v/v fetal calf serum (FCS, PAA) and 1% v/v Penicillin/Streptamycin (Gibco). Cells were grown in 80 cm2 cell culture flasks (NUNC) using 15 ml growth medium. Both cell lines were incubated under humidified atmosphere at +37° C. and 5% v/v $CO^2$. Cells were splitted when a confluency of approximately 90% was reached. Usually a splitting ratio of 1:5 or 1:10 was applied. For this purpose, supernatant was removed and cells were washed using 10 ml Dulbecco's Phosphate Buffered Saline (DPBS, Gibco). Cells were harvested by addition of 3 ml Trypsin/EDTA (Gibco) followed by an incubation of 5 to 10 min at +37° C. Successful detachment of cells was checked under the microscope (IMT-2, Olympus) and 7 ml growth medium were added. Cell number and viability were determined by trypanblue exclusion performed by using an automated cell analyzer (CEDEX, Innovatis). For this, 950 µl DPBS and 50 µl cell-suspension were mixed and used for analysis.

Isolation of Primary Mouse Satellite Cells:

Muscle tissue was taken from male ICR mice and minced by using scissors and a scalpel. Following incubation in protease solution (Sigma, St. Lois) for 1 h at 37° C., remaining tissue clumps were dissociated by vigorousely pipetting and loaded onto a Percoll (Pharmacia) gradient (75%, 50%, 30%). After centrifugation for 20 min at 1250× g, cells were collected from the $2^{nd}$ interphase (99% satellite cells), washed and cultured at a cell density of $1 \times 10^5$ cells/ml in 6-well plates. See also Danoviz ewt al. Methods Mol Biol. 2012; 798: 21-52.

Mammalian Cell Cultures:

Adherent Cells:

A431 are epidermoid carcinoma cells, MCF-7 cells are epithelial cells, ECV-304 was derived from a urinary bladder carcinoma.

Suspension Cells:

TF-1 cells originate from bone marrow of a patient with severe pancytopenia. These cells require medium supplemented with 5 ng/ml GM-CSF and differentiate into macrophages like cells. The Jurkat cell line was derived from the blood of a 14-year old boy with acute T-cell leukemia (ATCC). 711-3 is a human lymphoblastoid B-cell line.

1.4 AlamarBlue™ Assay

Proliferation was measured using the AlamarBlue™ assay according to the manufacturer's protocol. Briefly, $1 \times 10^4$ cells were seeded per well containing 100 µl growth medium. Cells were incubated over night at +37° C., 5% v/v $CO^2$ and humidified atmosphere. Prior performing the assay, viability of cells was checked under the microscope. Usually cells reached 60% confluence. Cells were washed three times with 100 µl DPBS per well. Peptides were diluted as desired (range 50 ng/ml to 20 µg/ml) in DMEM and 100 µl/well were added to the cells. Finally, cells were incubated at +37° C. for various time points depending on the type of experiment. Subsequently 10 µl/well AlamarBlue™ reagent (Invitrogen) was added. Plates were incubated for one hour at +37° C. Fluorescence (Ex. 570 nm, Em. 585 nm) was measured using a Varioskan Flash multi-plate reader (Thermo Scientific). Data were evaluated using Microsoft Excel and GraphPad Prism V4.

1.5 Hen's Egg Test—Chorionallantoic Membrane (HET-CAM) Assay

Fertilized specific-pathogen free eggs (White Leghorn) were obtained from BAXTER Biosciences (Vienna, Austria) on embryonic day 5 (E5). Eggs were disinfected on the surface using a towel soaked with Microzid (Schlilke, Austria). A tiny hole was drilled and 3 ml albumen were removed using a syringe equipped with a 18 G needle. Subsequently, the hole was covered with paraffin. To open the eggs, another hole was drilled on top. The egg shell was removed in this area using a pair of tweezers. The underlying membrane was removed resulting in the accessibility of the chorionallantoic membrane (CAM). This operational window was finally covered with sterile aluminium foil. Eggs were incubated at +37° C., 5% v/v $CO^2$ and humidified atmosphere. On embryonic day 6 (E6), a plastic foil (outer diameter 12 mm, inner diameter of 3 mm) was washed three times with 70% v/v ethanol and three times with sterile Locke (0.15M NaCl, 5 mM KCl, 2 mM CaCl2, 2 mM $NaHCO^3$) buffer. Finally, the plastic foil was laid onto the CAM. Selected peptides were diluted and applied onto the CAM on E6 by pipetting them in the middle of the plastic foil. Eggs were incubated at +37° C. until E8 or E11 depending on type of experiment. Pictures of the CAM were taken using a stereo microscope (StemiSV11, Zeiss, Germany) equipped with a digital camera (Coolpix990, Nikon, Japan) at defined time points. Angiogenic potential of tested peptides was evaluated microscopically at the end of the experiment.

1.6 Staining Methods

Trypan Blue staining is one of the most commonly used methods to determine the cell viability using light microscopy. Trypan blue can only stain cells if their membrane is damaged. Viable cells do not take up the dye.

1.7 Caspase 3—Specific ELISA

Caspase-3 is a member of the cysteine aspartic acid-specific protease family and is a marker of an early event in apoptosis. Caspase-3 expression was measured using a commercially available kit. Briefly, culture supernatants of cells undergoing apoptosis after different treatments were harvested and incubated with a substrate labeled with p-nitroaniline (pNA), which produces a yellow color when it is cleaved by caspase-3. The amount of produced yellow color is proportional to the caspase-3 activity, which can be determined by an ELISA reader at 405 nm (Promega). The assay was performed essentially as described by the manufacturer (instruction manual of CaspACE™ Assay System, Promega).

Example 2

Results

Recombinant SERF2 protein was cloned and expressed from a human cell line which resembles plasmacytoid dendritic cells. It has been shown that SERF2 both stimulated the proliferation of rat muscle cells and promotes angiogenesis. Therefore it is evident that SERF2 affects various human cells. A first experiment was set to find out, if SERF2 is able to stimulate proliferation of muscle cells and satellite cells.

2.1 SERF2 Supports Proliferation of Skeletal Muscle Cells, Cardiomyocytes and Primary Satellite Cells The aim of these experiments was to determine the proliferative effect of SERF2 on the rat embryonic cardiomyoblast cell line H9c2. Treatment was done for 24 h and an AlamarBlue™ assay performed as described in the methods section. Results obtained are shown in FIG. 3. A similar set of experiments was performed on mouse satellite cells MuMa23/P1 Results obtained are shown in FIG. 4. In both sets of experiments, treatment with human SERF2 resulted in a proliferative effect in a dose-dependent manner. This observation is similar to an experiment with L6 rat skeletal muscle cells (FIG. 2). In these experiments both cell lines (L6 and H9c29) were treated once with SERF2. An AlamarBlue™ assay was performed daily until day six of incubation. The results of this experiment are shown in FIG. 5 and FIG. 6 respectively.

SERF2 exerted a proliferative effect on L6 rat skeletal muscle cells in a dose- and time-dependent manner. The maximum effect was observed after three to six days of incubation. A similar result was obtained when cardiomyoblasts (H9c2) cells were treated with SERF2. A proliferative effect was observed peaking at 5 µg/ml SERF2.

2.2 SERF2 Exerts an Angiogenic Effect in Chicken CAM Assays

The HET-CAM assay enables the assessment of the angiogenic potential of substrates or cells. A suitable VEGF concentration was determined, which can be used as positive control. To achieve this, VEGF-A was applied onto the CAM of two eggs (100 ng/CAM abs.) once. Two eggs were left untreated and served as negative control. Treatment was performed on embryonic day 6 (E6). Angiogenic response was determined on Ell by light microscopy. Photographs of this experiment are shown in FIG. 12.

To evaluate the pro-angiogenic properties of SERF2, the protein was subjected to Het-CAM assay. An amount of 3 µg of PBS and SERF2 peptide was applied per CAM. VEGF-A (0.5 µg/CAM) was used as positive control, PBS served as negative control. Treatment was performed on embryonic day 6 and 7. All dilutions were stored at +4° C. in between and allowed to equilibrate to room temperature prior application. Angiogenic responses were evaluated microscopically on E7 as well as on E8. Each treatment was carried out in triplicates. Pictures were taken for documentation on these two days (see FIG. 12). As determined by manual count of newly formed vessels, SERF2 exerted a pro-angiogenic response in the Het-CAM assay.

2.3 SERF2 Prevents Apoptosis in Human Cells

The question was asked whether SERF2 has an effect on growth factor deprivation- or stress-induced apoptosis. The experimental protocol included addition of Hydrogen peroxide ($H_2O_2$), which is known to cause cellular stress and consequently apoptotic death in doses below 200 µM (Cox A., Carcinogenesis. 2007, Vol. 28, 10). Furthermore apoptosis was induced by deprivation of granulocyte macrophage colony-stimulating factor (GM-CSF) in cultures of TF-1 cells. These cells are dependent on the presence of a growth factor which is absolutely necessary for growth and differentiation of TF-1 cells.

Results are shown in FIGS. 7 (A431 cells—$H_2O_2$ assay), 8 (MCF-7 cells—$H_2O_2$ assay), 9 (Jurkat cells—$H_2O_2$ assay), 10 (TF-1 cells-growth factor assay) and 11 (711-3 cells—$H_2O_2$ assay).

In all experimental designs, the presence of SERF2 in cell cultures markedly reduced apoptosis. It is noteworthy that this effect was seen in cells of various origin, i.e. epithelial cells or cells of the myeloid or lymphoid lineage.

2.4. In Vivo Effects of SERF2 in Zebrafish.

The zebrafish has become an important model to study vertebrate development, physiology, and human diseases. With respect to the circulatory system, the zebrafish not only has highly conserved pathways governing hematopoiesis, vasculogenesis and angiogenesis compared to mammals, it shares all major blood cell types with them. Therefore, the zebrafish is an excellent model organism in which to study vertebrate cardiovascular development. Largescale forward genetic screens have identified many zebrafish mutants modeling hereditary blood diseases, malignant hematologic disorders, developmental hematology, as well as altered heart development and cardiac function. Another advantage of the zebrafish model is that simple diffusion supplies oxygen to the embryo during the first ten days of development. Thus, embryos can survive and develop normally during this period with no heartbeat or circulating blood, which facilitates the study of the development of the circulatory system.

Given the tiny size of their larvae, several methods to calculate cardiovascular performance, angiogenetic processes, muscle function and integrity of motoneurons were developed over the last decade. We have used zebrafish for in vivo characterization of SERF2 using two application routes: 1) Injection of the native protein into the yolk sac of 3 day post fertilization (dpf) animals or 2) chronic incubation with the native protein to supply it via diffusion. The efficient uptake of the protein by both routes of administration allowed to investigate its effect on cardiac muscle growth, angiogenesis and apoptosis.

Method.

SERF2 was administered by a) injection of the native protein into the yolk sac of 3 day post fertilization (dpf) animals and freshly fertilized eggs (2-8 cell stage) in various protein concentrations or chronic incubation with the native protein to supply it via diffusion. For in deep analysis of angiogenic effects flk-1 transgenic animals with gfp (green fluorescent protein) labelled endothelium were used. For all other experiments wildtype (wdt) animals were used.

Heart size was determined by measurement of end diastolic dimensions and calculation of end diastolic volume as described by Schwerte et al. (Schwerte et al. *The Journal of Experimental Biology.* 2003; 206 (Pt 8):1299-1307).

Vascularization Index.

A cast of the vascular bed was obtained by accumulation of the shifting vectors of moving erythrocytes from a number of subsequent difference pictures, as described previously (by Schwerte et al., supra). In parallel to this flk-1 transgenic animals, which show green fluorescing endothelium, were imaged.

TUNEL Assay for In Situ Staining of Apoptotic Cells

Apoptotic. cells were detected by TUNEL technology using in situ Cell Death Detection Kit, Fluorescein (Roche Applied Science, Mannheim, Germany) according to the manufacturer's instructions. Statistical Analysis. The acquired data statistically analyzed by using a two tailed students t-Test (Microsoft Excel) and significance was accepted when P<0.05. Data are presented as mean±S.E.M.

CONCLUSIONS

Treatment of zebrafish with SERF2 resulted in a significant increase of the animals heart volume. (see FIGS. 13*a* & 13*b*). One of the most prominent findings was the high and significant increase in blood cell concentration by 50 to 100% compared to controls (FIG. 14). Having in mind that this parameter is known from former studies to be more sensitive to physiological situations where increased oxygen delivery is needed, it may be a hint for increased vessel growth in later stages of zebrafish development than as already shown (Schwerte et al., supra). In vertebrates, blood vessels and blood cells have a common stem cell, the so called hemangioblast. It is known from the literature (Schwerte et al., supra) that the first response on hypoxia is an increased blood cell concentration before new vessels develop. From the physiological point of view this makes sense, because an increase in overall oxygen carrying capacity provides a faster response compared to newly developed vessels, which in turn have also to be filled with new blood and blood cells as well. Blood cell concentration is a central parameter in adjusting oxygen carrying capacity. In former studies it was shown that this parameter is more sensitive for physiological situations, where increased oxygen delivery is needed compared to vessel growth. At 7 dpf all but one treatment group show significantly increased blood cell concentrations. This increase was found in all drug delivery routes giving evidence that SERF2 can be delivered by both, incubation and uptake over the skin and injection and uptake over the gut (FIG. 15-17).

The reduced number of apoptotic cells in SERF2 treated animals reveals an obvious antiapoptotic effect of SERF2 in vivo (FIG. 18).

The invention claimed is:

1. A method of treating or preventing an atrophy disease or condition in a patient or method for cell regenerative therapy in a patient comprising the administration of a SERF2 protein, a nucleic acid encoding SERF2, or a cell recombinantly expressing SERF2 to the patient wherein said disease or condition characterized by oxidative stress, and the method comprises treating cells suffering from oxidative stress of the patient.

2. The method according to claim 1, wherein said atrophy is associated with an increased apoptosis or reduced regeneration of cells.

3. The method according to claim 1, wherein said atrophy is a reduction of cells selected from the group of muscle cells, heart muscle cells or skeletal muscle cells or smooth muscle cells, a connective tissue cell a cell of connective tissue surrounding a muscle, epithelial cells, blood vessel cells, and satellite cells or bone cells.

4. The method according to claim 1, wherein said disease or condition comprises oxidative stress in sarcopenia, muscular dystrophy, hypoplasia, cardiomyopathy, skin aging; or the method comprises preventing muscle loss or muscle dystrophy after a time in a surgical cast or any other immobility, or any combination thereof.

5. The method according to claim 1, wherein SERF2 is administered to a patient.

6. The method according to claim 1, wherein cells of a patient are treated ex vivo with SERF2 and said cells are administered to said patient.

7. The method according to claim 6, wherein stem cells or progenitor cells are administered to said patient.

8. The method according to claim 1, wherein said disease or condition is chronic or acute.

9. A method of increasing the proliferation of cells or protecting cells from oxidative stress, wherein said cells suffer from oxidative stress, and the method comprising administration of SERF2 or SERF2 encoding nucleic acids to said cells.

10. The method of claim 9, wherein said cells are selected from the group of stem cells, progenitor cells, mesenchymal cells, cardiomyocytes, satellite cells, hematopoietic stem cells or progenitor cells, muscle cells, heart muscle cells or skeletal muscle cells or smooth muscle cells, a connective tissue cell, a cell of connective tissue surrounding a muscle, and stem cells, progenitor cells, satellite cells, hematopoietic cells, skeletal muscle cells, epithelial cells, epidermal skin cells or a bone cell.

11. The method of claim 9, wherein the SERF2 comprises or consists of an amino acid sequence as set forth in SEQ ID NO: 1, or an amino acid sequence that has at least 70% sequence identity with the sequence as set forth in SEQ ID NO: 1.

12. The method of claim 9, wherein the administered SERF2 concentration is from 0.5 µg/ml to 1000 µg/ml, 1 µg/ml to 800 µg/ml, 2.5 µg/ml to 500 µg/ml, 4 µg/ml to 300 µg/ml, or 5 µg/ml to 100 µg/ml.

13. A pharmaceutical composition comprising SERF2 or SERF2 encoding nucleic acids and a pharmaceutically acceptable diluent, carrier, solubilizer, emulsifier, preservative, stabilizer and/or adjuvant, wherein the composition is lyophilized or in a hydrogel.

14. The method according to claim 1, wherein the SERF2 comprises or consists of an amino acid sequence as set forth in SEQ ID NO: 1, or an amino acid sequence that has at least 70% sequence identity with the sequence as set forth in SEQ ID NO: 1.

15. The method according to claim 1, wherein the administered SERF2 concentration is from 0.5 µg/ml to 1000 µg/ml, 1 µg/ml to 800 µg/ml, 2.5 µg/ml to 500 µg/ml, 4 µg/ml to 300 µg/ml, or 5 µg/ml to 100 µg/ml.

* * * * *